(12) United States Patent
Umehara et al.

(10) Patent No.: US 10,894,058 B2
(45) Date of Patent: Jan. 19, 2021

(54) METHOD FOR PRODUCING SOLID DISPERSION CONTAINING HARDLY SOLUBLE POLYPHENOL

(71) Applicant: KAO CORPORATION, Tokyo (JP)

(72) Inventors: Masahiro Umehara, Sumida-ku (JP); Akihiro Uda, Edogawa-ku (JP); Tetsuya Abe, Edogawa-ku (JP); Yasushi Yamada, Narita (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/506,939

(22) PCT Filed: Aug. 19, 2015

(86) PCT No.: PCT/JP2015/073271
§ 371 (c)(1),
(2) Date: Feb. 27, 2017

(87) PCT Pub. No.: WO2016/031651
PCT Pub. Date: Mar. 3, 2016

(65) Prior Publication Data
US 2017/0273999 A1    Sep. 28, 2017

(30) Foreign Application Priority Data

Aug. 29, 2014 (JP) ................................. 2014-176366

(51) Int. Cl.

| | | |
|---|---|---|
| *A61K 31/7048* | (2006.01) | |
| *A61K 8/73* | (2006.01) | |
| *A61Q 19/02* | (2006.01) | |
| *A61K 8/49* | (2006.01) | |
| *A61Q 15/00* | (2006.01) | |
| *A61Q 7/00* | (2006.01) | |
| *A61Q 19/10* | (2006.01) | |
| *A61Q 17/04* | (2006.01) | |
| *A61Q 5/02* | (2006.01) | |
| *A61K 8/60* | (2006.01) | |
| *A61K 47/26* | (2006.01) | |
| *A61K 47/36* | (2006.01) | |
| *A61K 31/732* | (2006.01) | |
| *B01F 3/22* | (2006.01) | |
| *A61K 9/14* | (2006.01) | |

(52) U.S. Cl.
CPC .......... *A61K 31/7048* (2013.01); *A61K 8/498* (2013.01); *A61K 8/60* (2013.01); *A61K 8/73* (2013.01); *A61K 31/732* (2013.01); *A61K 47/26* (2013.01); *A61K 47/36* (2013.01); *A61Q 5/02* (2013.01); *A61Q 7/00* (2013.01); *A61Q 15/00* (2013.01); *A61Q 17/04* (2013.01); *A61Q 19/02* (2013.01); *A61Q 19/10* (2013.01); *B01F 3/2284* (2013.01); *A61K 9/146* (2013.01)

(58) Field of Classification Search
CPC ................................................ A61K 31/7048
See application file for complete search history.

(56) References Cited

U.S. PATENT DOCUMENTS

| | | | |
|---|---|---|---|
| 4,610,890 A | 9/1986 | Miller et al. | |
| 4,707,367 A | 11/1987 | Miller et al. | |
| 4,820,534 A | 4/1989 | Saleeb et al. | |
| 4,999,205 A | 3/1991 | Todd, Jr. | |
| 5,456,923 A | 10/1995 | Nakamichi et al. | |
| 5,786,017 A | 7/1998 | Blake et al. | |
| RE37,860 E | 9/2002 | Blake et al. | |
| 6,462,093 B1 | 10/2002 | Miyamoto et al. | |
| 2005/0069628 A1 | 3/2005 | Goto et al. | |
| 2007/0021449 A1 | 1/2007 | Heeres et al. | |
| 2010/0034810 A1 | 2/2010 | Heeres et al. | |
| 2012/0108590 A1* | 5/2012 | Birtalan ............... | A61K 9/2027 514/234.5 |
| 2013/0303628 A1 | 11/2013 | Breitenbach et al. | |
| 2015/0148331 A1 | 5/2015 | Birtalan et al. | |

(Continued)

FOREIGN PATENT DOCUMENTS

| | | |
|---|---|---|
| CN | 1089232 C | 8/2002 |
| CN | 102151270 A | 8/2011 |
| CN | 103237458 A | 8/2013 |

(Continued)

OTHER PUBLICATIONS

Kalia et al., "Solid Dispersions: An Approach Towards Enhancing Dissolution Rate", Int. J. Pharm. Pharm. Sci., 2011, vol. 3, No. 4, pp. 9-19 (Year: 2011).*
English language translation of WO 2014/030731, obtained from google.com/patents on Mar. 31, 2018 (Year: 2014).*
Hirasawa et al., "Physicochemical Characterization and Drug Release Studies of Naproxen Solid Dispersions Using Lactose as a Carrier", Chem. Pharm. Bull., 1998, vol. 46, No. 6, pp. 1027-1030.
International Search Report for PCT/JP2015/073271 dated Oct. 6, 2015.

*Primary Examiner* — Rei Tsang Shiao
(74) *Attorney, Agent, or Firm* — Birch, Stewart, Kolasch & Birch, LLP

(57) ABSTRACT

Provided is a method of producing a solid dispersion that can improve solubility of a hardly soluble polyphenol in water. Specifically, provided is a method of producing a solid dispersion containing an amorphous hardly soluble polyphenol, the method including the steps of: mixing (A) a hardly soluble polyphenol, (B) at least one selected from the group consisting of a plant-derived polysaccharide, a seaweed-derived polysaccharide, and a microorganism-derived polysaccharide, a plant-derived polypeptide, and a microorganism-derived polypeptide, and (C) at least one selected from the group consisting of a monosaccharide and a disaccharide, followed by melting of the mixture by heating; and solidifying the molten product by cooling.

5 Claims, 2 Drawing Sheets

(56) References Cited

U.S. PATENT DOCUMENTS

2015/0335673 A1* 11/2015 Yamada ............... A61P 9/10
514/27

FOREIGN PATENT DOCUMENTS

| | | |
|---|---|---|
| CN | 103282025 A | 9/2013 |
| JP | 61-63614 A | 4/1986 |
| JP | 61-502656 A | 11/1986 |
| JP | 63-24652 B2 | 5/1988 |
| JP | 3-97761 A | 4/1991 |
| JP | 9-507267 A | 7/1997 |
| JP | 2003-325127 A | 11/2003 |
| JP | 2010-132605 A | 6/2010 |
| JP | 2013-103899 A | 5/2013 |
| JP | 2013-536251 A | 9/2013 |
| JP | 2013-544804 A | 12/2013 |
| JP | 2014-503470 A | 2/2014 |
| JP | 2014-125461 A | 7/2014 |
| JP | 2014-144988 A | 8/2014 |
| WO | WO 86/00502 A1 | 1/1986 |
| WO | WO 92/18106 A1 | 10/1992 |
| WO | WO 96/11589 A1 | 4/1996 |
| WO | WO 97/06781 A1 | 2/1997 |
| WO | WO 2012/027731 A2 | 3/2012 |
| WO | WO 2012/049253 A1 | 4/2012 |
| WO | WO 2012/121758 A1 | 9/2012 |
| WO | WO 2014/030731 A1 | 2/2014 |
| WO | WO-2014030731 A1 * 2/2014 ........... A61K 31/192 |
| WO | WO 2014/104157 A1 | 7/2014 |

* cited by examiner

CRYSTALLINITY DEGREE 87%

CRYSTALLINITY DEGREE 52%

CRYSTALLINITY DEGREE 17%

METHOD FOR PRODUCING SOLID DISPERSION CONTAINING HARDLY SOLUBLE POLYPHENOL

FIELD OF THE INVENTION

The present invention relates to a method of producing a solid dispersion containing a polyphenol hardly soluble in water.

BACKGROUND OF THE INVENTION

Polyphenols are known to have antioxidative activities, and are expected to have, for example, anti-arteriosclerotic effect, anti-allergic effect, and augmentation effect of blood stream. Therefore, the polyphenols are recognized as important components of health foods and the like.

Meanwhile, since many of the polyphenols are hardly soluble in water, it is difficult to use them in foods and drinks. For example, ellagic acid has a solubility in water (25° C.) as low as 0.005 mg/mL, and hence is desired to have improved solubility in water.

Meanwhile, there is known a technology for preparing a solid dispersion by dispersing a hardly water-soluble functional substance particularly in an amorphous state in a water-soluble carrier to enhance solubility in water and body absorbability, resulting in improving effectiveness in the body.

As a method of preparing a solid dispersion, for example, there are given: a spray drying method involving dissolving a hardly water-soluble functional substance and a carrier in an organic solvent, and subjecting the resultant to spray drying; a mixing and pulverization method involving subjecting a hardly water-soluble functional substance to dry pulverization together with a carrier; and a heat-melting method involving melting a hardly water-soluble functional substance and a carrier by heating, and solidifying the resultant by cooling (for example, Patent Documents 1 and 2).

In Patent Document 1 described above, a solid dispersion is prepared by dissolving a pharmaceutical component, hydroxypropyl methylcellulose acetate succinate, and a wetting agent in an organic solvent, and subjecting the resultant to spray drying. In addition, in Patent Document 2, a solid dispersion is prepared by treating a pharmaceutical component, copovidone as a polymer carrier, a surfactant, and the like at high temperature, and loading the resultant in a screw-type extruding machine.

[Patent Document 1] JP-A-2013-536251
[Patent Document 2] JP-A-2013-544804

SUMMARY OF THE INVENTION

The present invention provides a method of producing a solid dispersion containing an amorphous hardly soluble polyphenol, the method including the steps of: mixing (A) a hardly soluble polyphenol, (B) at least one selected from the group consisting of a plant-derived polysaccharide, a seaweed-derived polysaccharide and a microorganism-derived polysaccharide, a plant-derived polypeptide, and a microorganism-derived polypeptide, and (C) at least one selected from the group consisting of a monosaccharide and a disaccharide, followed by melting of the mixture by heating; and solidifying the molten product by cooling.

The present invention provides a solid dispersion containing an amorphous hardly soluble polyphenol obtained by the above-mentioned production method.

The present invention provides a food and drink that contains the above-mentioned solid dispersion containing an amorphous hardly soluble polyphenol.

DETAILED DESCRIPTION OF THE INVENTION

Figure 1:
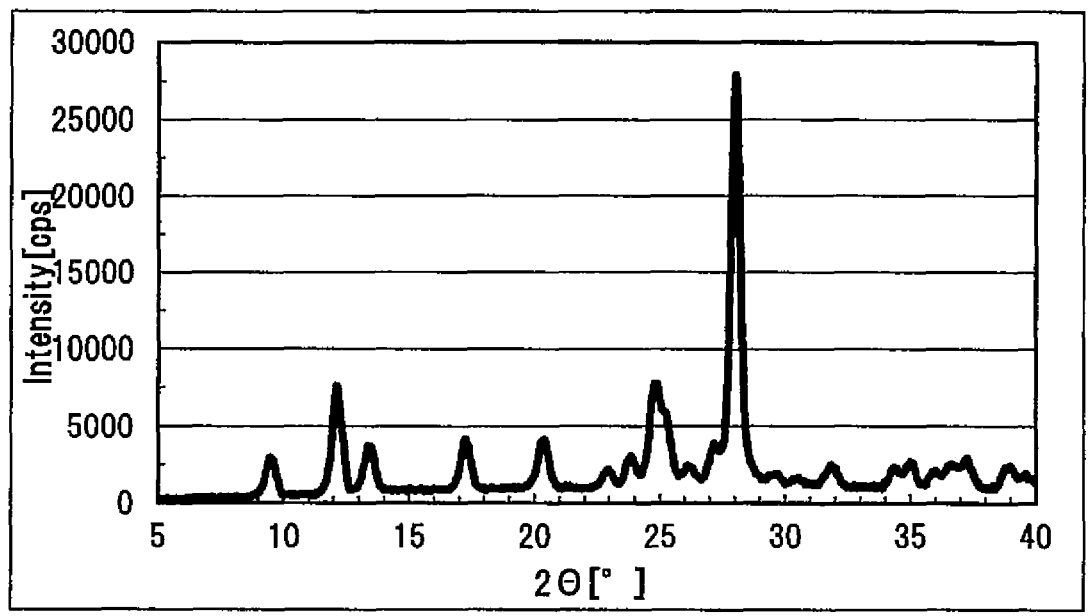
FIG. 1 is a graph for showing the results of powder X-ray diffraction for ellagic acid of Comparative Example 1.

A technology for preparing a solid dispersion is considered to be useful for improvement in solubility of a hardly soluble polyphenol, such as ellagic acid, in water.

Of the above-mentioned methods of preparing a solid dispersion, it is desirable to avoid the spray drying method using an organic solvent in view of use of a hardly soluble polyphenol in food applications because attention needs to be paid to a residual solvent. In addition, in the mixing and pulverization method, concern is raised about incorporation of foreign matters. Meanwhile, the heat-melting method is a technology that can avoid the use of an organic solvent and is advantageous from the viewpoint of facility load as compared to the spray drying method. However, the method is much restricted in use of a carrier in food applications, and hence, for example, the findings of Patent Document 2 cannot be applied as they are.

Accordingly, the present invention provides a method of producing a solid dispersion containing a hardly soluble polyphenol having improved solubility in water.

The inventors of the present invention made various investigations on technologies for preparing a solid dispersion of a hardly soluble polyphenol, such as ellagic acid, and found that when a hardly soluble polyphenol, at least one selected from the group consisting of predetermined polysaccharide and polypeptide, and at least one selected from the group consisting of a monosaccharide and a disaccharide are mixed in combination, melted by heating, and then solidified by cooling, a solid dispersion can be obtained in a state in which the hardly soluble polyphenol is dispersed in an amorphous state in the polysaccharide or polypeptide, and that the water solubility of a hardly soluble polyphenol in the solid dispersion is high, and the high water solubility can be maintained stably.

According to the present invention, there can be provided a solid dispersion containing a hardly soluble polyphenol having remarkably improved solubility in water. The solid dispersion of the present invention is suited for a food and drink because the solid dispersion is produced without using an organic solvent in production processes.

The present invention is directed to a method of producing a solid dispersion containing an amorphous hardly soluble polyphenol, the method including the steps of: mixing (A) a hardly soluble polyphenol, (B) at least one selected from the group consisting of a plant-derived polysaccharide, a seaweed-derived polysaccharide, and a microorganism-derived polysaccharide, a plant-derived polypeptide, and a microorganism-derived polypeptide, and (C) at least one selected from the group consisting of a monosaccharide and a disaccharide, followed by melting of the mixture by heating; and solidifying the molten product by cooling.

In this description, (A) the hardly soluble polyphenol is also referred to as "component (A)", (B) at least one selected from the group consisting of the plant-derived polysaccharide, the seaweed-derived polysaccharide, and the microorganism-derived polysaccharide, the plant-derived polypeptide, and the microorganism-derived polypeptide is also referred to as "component (B)", and (C) at least one selected from the group consisting of the monosaccharide and the disaccharide is also referred to as "component (C)".

The term "hardly soluble polyphenol" as used herein refers to a polyphenol having a solubility in water at 25° C. of 5 g/L or less.

In the present invention, a polyphenol having a solubility in water at 25° C. of preferably 2 g/L or less, more preferably 1 g/L or less, more preferably 0.5 g/L or less, even more preferably 0.1 g/L or less may be applied. In this description, the term "solubility" refers to the number of gram (s) of a solute dissolved in 1 L of a solution, and is represented by the unit of [g/L].

As (A) the hardly soluble polyphenol, a phenolic substance in which preferably one or more, more preferably two or more hydroxyl groups are substituted on a benzene ring may be applied. Examples thereof include flavonoid, tannin, and phenol acid, each derived from plants. Examples of the hardly water-soluble polyphenol that may be more preferably applied include flavonols, flavanones, flavones, isoflavones, anthocyanidins, hydroxycinnamic acid derivatives, ellagic acid, lignan, and curcumins.

Specific examples thereof include: flavonols, such as quercetin, fisetin, rutin, quercitrin, isoquercitrin, myricitrin, and myricetin; flavanones, such as hesperidin, neohesperetin, hesperetin, naringin, and naringenin; flavones, such as sudachitin, ringenin, prunin, astragalin, kaempferol, apiin, apigenin, and nobiletin; isoflavones, such as soy isoflavone, daidzein, daidzin, glycitein, glycitin, genistein, and genistin; anthocyanidins, such as delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, and callistephin; hydroxycinnamic acid derivatives, such as phenol carboxylic acids and resveratrol; ellagic acid; lignans, such as sesamin; and curcumins, such as curcumin. Examples of the phenol carboxylic acids include ferulic acid, caffeic acid, and p-coumaric acid. Of those, ellagic acid, quercetin, ferulic acid, curcumin, sesamin, soy isoflavone, resveratrol, nobiletin, and naringenin are preferred, and ellagic acid is more preferred.

The hardly soluble polyphenols may be used alone or as a mixture of two or more thereof. In addition, when a salt or a hydrate is present in the hardly soluble polyphenols, the hardly soluble polyphenols may contain the salt or the hydrate.

Ellagic acid is a compound having a polyphenol structure represented by a molecular formula $C_{14}H_6O_8$. It is known that many ellagic acid compounds contained in a plant are present in a state in which a saccharide referred to as ellagitannin is bonded thereto. In the present invention, not such ellagic acid that is in a state in which a saccharide is bonded thereto but an ellagic acid that is present in a free state is preferably used.

As commercially available ellagic acid, there may be given, for example, pomegranate ellagic acid (Sabinsa Japan Corporation), ellagic acid dihydrate (Wako Pure Chemical Industries, Ltd.), and ellagic acid (KANTO CHEMICAL CO., INC.).

As (B) the plant-derived, seaweed-derived, or microorganism-derived polysaccharide used in the present invention, there may be preferably applied an acidic polysaccharide, a neutral polysaccharide, or a basic polysaccharide that has properties due to its structure when dissolved in a water-based solvent. The acidic polysaccharide or the neutral polysaccharide may be preferably applied as the polysaccharide, and the acidic polysaccharide may be more preferably applied as the polysaccharide.

Examples of the acidic polysaccharide include pectin, potassium alginate, sodium alginate, gum arabic, xanthan gum, gellan gum, tragacanth gum, inulin, λ-carrageenan, ι-carrageenan, κ-carrageenan, polygalacturonic acid, agar, porphyran, funoran, and furcellaran.

Examples of the neutral polysaccharide include tamarind seed gum, guar gum, locust bean gum, starch, pullulan, laminaran, and glucomannan.

An example of the basic polysaccharide is chitosan.

Of those, pectin, potassiumalginate, sodiumalginate, inulin, λ-carrageenan, and polygalacturonic acid are preferred, and pectin is more preferred.

Pectin is a polysaccharide including galacturonic acid as a major component, and has a weight-average molecular weight of preferably 260,000 or less, more preferably 230,000 or less, even more preferably 210,000 or less, from the viewpoint of solubility of the component (A). In addition, the weight-average molecular weight is preferably 30,000 or more, more preferably 100,000 or more, even more preferably 150,000 or more, from the viewpoint of suppressing crystallization of the component (A). (B) Pectin has a weight-average molecular weight of preferably from 30,000 to 260,000, more preferably from 30,000 to 230,000, more preferably from 100,000 to 210,000, even more preferably from 150,000 to 210,000.

The term "weight-average molecular weight" as used herein refers to a value measured by gel permeation chromatography (GPC) unless otherwise specified. Measurement of the weight-average molecular weight of pectin by GPC is carried out in accordance with a method described in Examples below.

In general, pectin is classified into LM pectin having an esterification rate of less than 50% and HM pectin having an esterification rate of 50% or more. The esterification rate of pectin is defined by the following equation (1).

Esterification rate (%)=(Methyl galacturonate (mol))/ (Total galacturonic acid (mol))×100    Equation (1)

The esterification rate may be measured by, for example, a method of Inari and Takeuchi (Nippon Shokuhin Kagaku Kogaku Kaishi, 44, 319-324 (1997)).

In the present invention, both of the LM pectin and the HM pectin are preferred, and from the viewpoint of ease in preparation of the solid dispersion containing an amorphous hardly soluble polyphenol, HM pectin having an esterification rate of 50% or more is more preferred, and HM pectin having an esterification rate of 60% or more is even more preferred. The esterification rate of pectin refers to an esterification rate of the entire pectin compound used. When a plurality of pectin compounds are used, the esterification rate is calculated by dividing, by the total mass of the pectin compounds, a sum of products each determined by multiplying the mass of each pectin compound by an esterification rate determined by the equation (1).

As (B) the plant-derived polypeptide and the microorganism-derived polypeptide used in the present invention, there may be given, for example, soy protein, wheat protein, rice protein, and polyglutamic acid. In addition, partially decomposed products thereof may be used.

Of those, soy protein is preferred because the soy protein is rich in essential amino acids.

The components (B) may be used alone or as a mixture of two or more thereof.

As (C) the monosaccharide and the disaccharide used in the present invention, those each having a melting point lower than the melting point of the component (B) and each having a lowering effect on the softening temperature of the component (B) may be preferably applied.

Examples thereof include: disaccharides, such as sucrose, maltose, trehalose, and lactose; and monosaccharides, such as glucose, fructose, and galactose. The saccharides may be used alone or in combination of two or more thereof.

Of those, maltose, fructose, and glucose are preferred because they have low softening points and hence can be processed easily. The saccharides may be anhydrates or hydrates.

In the present invention, the solid dispersion containing amorphous ellagic acid is produced using preferably pectin as the component (B), and one or two or more selected from the group consisting of a monosaccharide and a disaccharide as the component (C), more preferably maltose or fructose as the component (C), from the viewpoint of solubility of ellagic acid in water.

In the present invention, the component (A), the component (B), and the component (C) are mixed, and heating is carried out to melt the mixture.

In mixing of the component (A), the component (B), and the component (C), the content of the component (A) in the mixture is preferably 5 mass % or more, more preferably 15 mass % or more, more preferably 20 mass % or more, more preferably 25 mass % or more, more preferably 30 mass % or more, more preferably 35 mass or more, even more preferably 40 mass % or more, from the viewpoint of increasing the content of the hardly soluble polyphenol in the solid dispersion, and is preferably 75 mass % or less, more preferably 50 mass % or less, even more preferably 45 mass % or less, from the viewpoint of facilitating processing. In addition, the content of (A) the hardly soluble polyphenol in the mixture is preferably from 5 mass % to 75 mass %, more preferably from 15 mass % to 50 mass %, more preferably from 20 mass % to 50 mass %, more preferably from 25 mass % to 50 mass %, more preferably from 30 mass % to 50 mass %, more preferably from 35 mass % to 50 mass %, more preferably from 40 mass to 50 mass %, even more preferably from 40 mass % to 45 mass %.

The content of the component (B) varies depending on the kind thereof, and the content of the component (B) in the mixture is preferably 5 mass % or more, more preferably 10 mass % or more, more preferably 15 mass % or more, even more preferably 25 mass % or more, from the viewpoint of solubility of the hardly soluble polyphenol in water, and is preferably 90 mass % or less, more preferably 85 mass % or less, more preferably 80 mass % or less, more preferably 70 mass % or less, more preferably 65 mass % or less, even more preferably 50 mass % or less, from the viewpoint of facilitating preparation of the solid dispersion. In addition, the content of the component (B) in the mixture is preferably from 5 mass % to 90 mass %, more preferably from 10 mass % to 90 mass %, more preferably from 15 mass % to 85 mass %, more preferably from 15 mass % to 80 mass %, more preferably from 25 mass % to 70 mass %, more preferably from 25 mass % to 65 mass %, even more preferably from 25 mass % to 50 mass %.

The content of the component (C) varies depending on the kind thereof, and the content of the component (C) in the mixture is preferably 5 mass % or more, more preferably 10 mass % or more, from the viewpoints of solubility of the hardly soluble polyphenol in water and facilitating the preparation of the solid dispersion, and is preferably 85 mass % or less, more preferably 50 mass % or less, even more preferably 30 mass % or less, from the viewpoint of increasing solubility of the solid dispersion in water and the content of the hardly soluble polyphenol. In addition, the content of the component (C) in the mixture is preferably from 5 mass to 85 mass %, more preferably from 10 mass % to 50 mass %, even more preferably from 10 mass % to 30 mass %.

In the mixing of the component (A), the component (B), and the component (C), the mass ratio of the component (C) to the component (A), [(C)/(A)], is preferably 0.2 or more, more preferably 0.3 or more, from the viewpoint of facilitating the preparation of the solid dispersion. In addition, the mass ratio is preferably 19 or less, more preferably 17 or less, more preferably 9 or less, more preferably 6 or less, even more preferably 2 or less, from the viewpoint of increasing the solubility of the hardly soluble polyphenol in water. In addition, the mass ratio is preferably from 0.2 to 19, more preferably from 0.2 to 17, more preferably from 0.2 to 9, more preferably from 0.3 to 6, even more preferably from 0.3 to 2.

In the mixing of the component (A), the component (B), and the component (C), the mass ratio of the component (C) to the component (B), [(C)/(B)], is preferably 0.05 or more, more preferably 0.06 or more, more preferably 0.08 or more, even more preferably 0.11 or more, from the viewpoint of facilitating the preparation of the solid dispersion. In addition, the mass ratio is preferably 100 or less, more preferably 17 or less, more preferably 4 or less, even more preferably 2 or less, from the viewpoint of increasing the solubility of the hardly soluble polyphenol in water. In addition, the mass ratio is preferably from 0.05 to 100, more preferably from 0.05 to 17, more preferably from 0.08 to 4, even more preferably from 0.11 to 2.

In the mixing of the component (A), the component (B) and the component (C), the mass ratio of the component (A) to the total of the component (B) and the component (C), [(A)/{(B)+(C)}], is preferably 0.05 or more, more preferably 0.06 or more, more preferably 0.1 or more, even more preferably 0.17 or more, from the viewpoint of increasing the content of the component (A) in the solid dispersion. In addition, the mass ratio is preferably 3.3 or less, more preferably 3 or less, more preferably 1.1 or less, even more preferably 0.47 or less, from the viewpoint of solubility of the component (A) in water. In addition, the mass ratio is preferably from 0.05 to 3.3, more preferably from 0.06 to 3, more preferably from 0.1 to 1.1, even more preferably from 0.17 to 0.47.

A method of melting the mixture of the component (A), the component (B), and the component (C) by heating is not particularly limited, and a known method is applicable thereto. A method involving melting the mixture by heating with stirring is preferred. For example, kneading machine and extruding machine, such as an extruder and a kneader, may be used. In addition, stirring machine, such as a ribbon mixer, may be used. Examples thereof include an extruder manufactured by HAAKE, an extruder manufactured by Thermo Scientific, KZW 134T manufactured by Technovel Corporation, KRC kneader manufactured by Kurimoto Ltd., MIRACLE K.C.K manufactured by Asada Iron Works. Co., Ltd. EA-20 manufactured by Suehiro EPM Corporation, and MC-1102 manufactured by N. P. & Company Inc. As heating means, there are given, for example, water vapor and electricity.

Of those, an extruding machine including a screw, which can perform kneading and heat-melting simultaneously, is preferably used from the standpoint of preparation of a solid dispersion having uniform composition. The extruding machine including a screw may be a single screw extruding machine or a twin screw extruding machine, and the twin screw extruding machine is preferred from the standpoint of, for example, enhancing conveying capacity. The twin screw extruding machine preferably has two screws that are rotatably inserted inside a cylinder, and any conventionally known extruding machine may be used. The rotation of the two screws may be in the same direction or in the opposite directions. In order to enhance the conveying capacity, the rotation in the same direction is preferred. In addition, as to the engagement condition of the screws, any type of the extruding machines, such as the types of complete engagement, partial engagement, and non-engagement, may be used. From the standpoint of improving processing capacity, the complete engagement type and the partial engagement type are preferred.

In addition, the extruding machine including a screw preferably includes a so-called kneading disc in any part of the screw from the standpoint of applying strong compressive and shear forces. The kneading disc, which includes a plurality of kneading discs, is formed by combining these discs while displacing their positions continuously by a certain phase, for example, by 90° each, and while rotating of the screw, the mixture of the component (A), the component (B), and the component (C) is forcibly passed through a narrow space, and hence an extremely strong shear force can be applied thereto. The screw is preferably constructed in such a way that the kneading disc and a plurality of the screw segments are arranged alternately. In the case of the twin screw extruding machine, it is preferred that these two screws have the same structure.

When the extruding machine including a screw is used, a continuous treatment method involving loading a mixture of the component (A), the component (B), and the component (C), preferably a product obtained by roughly pulverizing the mixture into the extruding machine, and rotating the screw is preferred.

The screw rotation speed of the extruding machine is preferably from 30 r/min to 500 r/min, more preferably from 50 r/min to 300 r/min, more preferably from 50 r/min to 250 r/min, even more preferably from 80 r/min to 200 r/min.

In addition, the shear rate of the extruding machine is preferably 10 sec$^{-1}$ or more, more preferably from 20 sec$^{-1}$ to 30,000 sec$^{-1}$, even more preferably from 50 sec$^{-1}$ to 3,000 sec$^{-1}$. The shear rate is preferably 10 sec$^{-1}$ or more because pulverization proceeds effectively.

The molten product obtained by melting in the extruding machine including a screw is extruded and molded.

As to the number of passes in the extruding machine, a sufficient effect may be achieved by one pass. It is preferred to carry out two or more passes from the viewpoint of improving dispersibility of the component (A). In addition, in view of the productivity, the number is preferably from 1 to 10. By repeating the pass, coarse particles are pulverized and hence a solid dispersion containing the component (A), which has a small variation in particle size, can be obtained. When two or more passes are carried out, in view of the producing capacity, the treatment may be done by arranging a plurality of extruding machines in series.

A heating temperature is a temperature equal to or higher than the softening point of the component (B), preferably a temperature equal to or higher than the melting point of the component (B). In the present invention, the term "softening point" refers to a temperature at which a solid substance starts softening and deforming by heating of the substance. When the component (B) softens or melts by heating, the component (A) melts there.

For example, in the case of pectin, it typically has a melting point of 151° C. When the component (C) having a melting point lower than the melting point of pectin melts, pectin melts at a temperature lower than 151° C. owing to its compatibility.

In the present invention, the heating temperature is preferably 75° C. or more, more preferably 100° C. or more, more preferably 115° C. or more, even more preferably 120° C. or more, from the viewpoint that heat treatment is preferably carried out at a temperature equal to or higher than the temperature at which the component (B) or the component (C) softens, and the heating temperature is preferably 250° C. or less, more preferably 200° C. or less, more preferably 180° C. or less, more preferably 175° C. or less, even more preferably 165° C. or less, from the viewpoint of thermal stability of the hardly soluble polyphenol. In addition, the heating temperature is preferably from 75° C. to 250° C., more preferably from 100° C. to 200° C., more preferably from 115° C. to 180° C., more preferably from 115° C. to 175° C., more preferably from 115° C. to 165° C., even more preferably from 120° C. to 165° C.

In addition, when maltose is used as the component (C), the heating temperature is preferably 75° C. or more, more preferably 100° C. or more, even more preferably 115° C. or more.

In addition, when fructose is used as the component (C), the heating temperature is preferably 75° C. or more, more preferably 85° C. or more, even more preferably 100° C. or more.

In addition, when glucose is used as the component (C), the heating temperature is preferably 75° C. or more, more preferably 100° C. or more, more preferably 120° C. or more, more preferably 140° C. or more, even more preferably 150° C. or more.

The upper limit of the heating temperature is preferably 250° C. or less, more preferably 200° C. or less, more preferably 175° C. or less, even more preferably 165° C. or less, as mentioned above.

A heating time is preferably 30 minutes or less, more preferably 15 minutes or less, even more preferably 10 minutes or less after the temperature of the mixture reaches a temperature at which the component (B) melts, from the viewpoints of improvement in solubility of the hardly soluble polyphenol in water, thermal stability, and productivity. In addition, the heating time is preferably 1 minute or more, more preferably 3 minutes or more, even more preferably 5 minutes or more, from the viewpoint of the solubility of the hardly soluble polyphenol in water. Further, the heating time is preferably from 1 minute to 30 minutes, more preferably from 3 minutes to 15 minutes, even more preferably from 5 minutes to 10 minutes after the temperature of the mixture reaches the temperature at which the component (B) melts.

Subsequently, the resultant molten product is solidified by cooling. The hardly soluble polyphenol becomes amorphous by the treatment, and hence a solid dispersion containing the hardly soluble polyphenol in an amorphous state is obtained.

The term "amorphous" refers to a state in which a substance is lack of certain regularity in its molecular array. The state of "amorphous" may be confirmed by powder X-ray diffraction.

In the present invention, the amorphous hardly soluble polyphenol, depending on the kind thereof, has a crystallinity degree of preferably 50% or less, more preferably 40% or less, more preferably 20% or less, more preferably 10% or less, even more preferably 0%, which means that the polyphenol is completely amorphous.

Amorphous ellagic acid has a crystallinity degree of 35% or less, preferably 20% or less.

When the solid dispersion of the present invention is subjected to powder X-ray diffraction measurement, no crystalline diffraction peak of the hardly soluble polyphenol is preferably detected.

The crystallinity degree of the hardly soluble polyphenol may be calculated by the following method. First, diffraction intensity values determined by an X-ray diffraction method are subjected to peak separation into a crystalline diffraction line and an amorphous halo through profile fitting without considering effects of incoherent scattering, a lattice defect, and the like. Next, the crystallinity degree of a hardly soluble polyphenol is calculated by the following calculation equation (2) from the resultant integrated intensities of the respective peaks:

$$\text{Crystallinity degree (\%) of hardly soluble polyphenol} = [\Sigma I\alpha/(\Sigma I\alpha + \Sigma Iam)] \times 100 \quad (2)$$

where $\Sigma I\alpha$ represents a sum of integrated intensities of respective peaks in a crystalline diffraction line, and $\Sigma Iam$ represents a sum of integrated intensities of respective peaks in a diffraction line of an amorphous part.

A temperature for cooling the molten product is a temperature lower than the temperature at which the component (B) melts, and is preferably 50° C. or less, more preferably 30° C. or less. The cooling is preferably carried out by, for example, a method involving placing the solid dispersion under an atmosphere at preferably 50° C. or less, more preferably 30° C. or less, even more preferably room temperature (25° C.). In addition, it is preferable to blow cold air to a solid dispersion after heat treatment to immediately cool the solid dispersion. The cooling rate of the solid dispersion, which is calculated from a time required for lowering the temperature of the heat treatment to 25° C., is preferably 0.1° C./s or more, more preferably 0.2° C./s or more, even more preferably 0.3° C./s or more, and is, from the standpoint of, for example, restriction on product ion facility, for example, preferably 100° C./s or less, more preferably 50° C./s or less. A cooling time is preferably 30 minutes or less, more preferably 20 minutes or less, more preferably 10 minutes or less, even more preferably 5 minutes or less.

The solid dispersion containing a hardly soluble polyphenol and having been solidified by cooling may be molded so as to have any shape and size, and examples thereof include a pellet and a granule. In addition, if necessary, the solid dispersion may be pulverized.

The solid dispersion containing an amorphous hardly soluble polyphenol obtained by the production method of the present invention is extremely excellent in solubility in water.

The solubility of the hardly soluble polyphenol in water (25° C.) in the solid dispersion is preferably 1.5 times or more, more preferably 5 times or more, more preferably 10 times or more, even more preferably 50 times or more, as high as that of an untreated hardly soluble polyphenol.

In addition, the solubility of ellagic acid in water (25° C.) in the solid dispersion is preferably 0.04 g/L or more (7.5 times or more as high as that of untreated ellagic acid), more preferably 0.12 g/L or more (22 times or more as high as that of untreated ellagic acid), even more preferably 0.2 g/L or more (37 times or more as high as that of untreated ellagic acid).

In addition, the content of water in the solid dispersion is preferably 20 mass or less, more preferably 10 mass % or less, more preferably 7 mass % or less, even more preferably 5 mass % or less, from the viewpoints of ease in pulverization of the solid dispersion and excellent handling ability.

The solid dispersion containing the amorphous hardly soluble polyphenol obtained by the production method of the present invention can be used in a variety of foods and drinks, pharmaceuticals, cosmetics, and the like. In particular, the solid dispersion is useful in water-based products.

Examples of the foods and drinks include liquid, solid, or semi-solid foods and drinks, such as drinks, breads, noodles, confectionery, e.g., a cookie, snacks, jellies, a dairy product, a frozen food, an instant food, e.g., powder coffee, a processed starch product, a processed meat product, any other processed food, a seasoning, and a nutritional supplement. In addition, examples of the pharmaceuticals include dosage forms, such as a tablet (e.g., a chewable tablet), a capsule, and a powder. In addition, examples of the cosmetics include a cleanser, a toning lotion, a cosmetic composition for make-up, a cosmetic composition for sunscreen, a cosmetic composition for pimples, a cosmetic composition for deodorant, a cosmetic composition for whitening, a hair wash, and a hair growth agent.

Embodiments and preferred embodiments of the present invention are described below.

<1> A method of producing a solid dispersion containing an amorphous hardly soluble polyphenol, the method comprising the steps of: mixing (A) a hardly soluble polyphenol, (B) at least one selected from the group consisting of a plant-derived polysaccharide, a seaweed-derived polysaccharide, and a microorganism-derived polysaccharide, a plant-derived polypeptide, and a microorganism-derived polypeptide, and (C) at least one selected from the group consisting of a monosaccharide and a disaccharide, followed by melting of the mixture by heating; and solidifying the molten product by cooling.

<2> The method of producing a solid dispersion according to Item <1>, wherein the component (A) is a polyphenol having a solubility in water at 25° C. of preferably 5 g/L or less, more preferably 2 g/L or less, more preferably 1 g/L or less, more preferably 0.5 g/L or less, even more preferably 0.1 g/L or less.

<3> The method of producing a solid dispersion according to Item <1> or <2>, wherein the component (A) is preferably one or two or more selected from the group consisting of flavonols, flavanones, flavones, isoflavones, anthocyanidins, hydroxycinnamic acid derivatives, ellagic acid, lignan, and curcumins.

<4> The method of producing a solid dispersion according to any one of Items <1> to <3>, wherein the component (A) is preferably one or two or more selected from the group consisting of ellagic acid, quercetin, ferulic acid, curcumin, sesamin, soy isoflavone, resveratrol, nobiletin, and naringenin.

<5> The method of producing a solid dispersion according to any one of Items <1> to <4>, wherein the component (B) is preferably one or two or more selected from the group consisting of an acidic polysaccharide, the plant-derived polypeptide, and the microorganism-derived polypeptide.

<6> The method of producing a solid dispersion according to any one of Items <1> to <5>, wherein the component (B) is preferably one or two or more selected from the group consisting of pectin, polyglutamic acid, potassium alginate, sodium alginate, inulin, λ-carrageenan, soy protein, and polygalacturonic acid.

<7> The method of producing a solid dispersion according to any one of Items <1> to <5>, wherein the component (B) is preferably pectin.

<8> The method of producing a solid dispersion according to Item <7>, wherein the weight-average molecular weight of (B) pectin is preferably 260,000 or less, more preferably 230,000 or less, even more preferably 210,000 or less, is preferably 30,000 or more, more preferably 100,000 or more, even more preferably 150,000 or more, and is preferably from 30,000 to 260,000, more preferably from 30,000 to 230,000, more preferably from 100,000 to 210,000, even more preferably from 150,000 to 210,000.

<9> The method of producing a solid dispersion according to Item <7> or <8>, wherein (B) pectin has an esterification rate of preferably 50% or more, more preferably 60% or more.

<10> The method of producing a solid dispersion according to any one of Items <1> to <9>, wherein (C) the monosaccharide and the disaccharide is preferably one or two or more selected from the group consisting of sucrose, maltose, trehalose, lactose, glucose, fructose, and galactose, more preferably one or two or more selected from the group consisting of sucrose, maltose, trehalose, lactose, glucose, fructose, and galactose, even more preferably one or two or more selected from the group consisting of maltose, glucose, and fructose.

<11> The method of producing a solid dispersion according to any one of Items <1> to <10>, wherein the component (A) is ellagic acid, the component (B) is pectin, and the component (C) is one or two or more selected from the group consisting of the monosaccharide and the disaccharide.

<12> The method of producing a solid dispersion according to any one of Items <1> to <11>, wherein the content of the component (A) in the mixture of the component (A), the component (B), and the component (C) is preferably 5 mass % or more, more preferably 15 mass % or more, more preferably 20 mass % or more, more preferably 25 mass % or more, more preferably 30 mass % or more, more preferably 35 mass % or more, even more preferably 40 mass % or more, is preferably 75 mass % or less, more preferably 50 mass % or less, even more preferably 45 mass % or less, and is preferably from 5 mass % to 75 mass %, more preferably from 15 mass % to 50 mass %, more preferably from 20 mass % to 50 mass %, more preferably from 25 mass % to 50 mass %, more preferably from 30 mass % to 50 mass %, more preferably from 35 mass % to 50 mass %, more preferably from 40 mass % to 50 mass %, even more preferably from 40 mass % to 45 mass %.

<13> The method of producing a solid dispersion according to any one of Items <1> to <12>, wherein the content of the component (B) in the mixture of the component (A), the component (B), and the component (C) is preferably 5 mass % or more, more preferably 10 mass % or more, more preferably 15 mass % or more, even more preferably 25 mass % or more, is preferably 90 mass % or less, more preferably 85 mass % or less, more preferably 80 mass % or less, more preferably 70 mass % or less, more preferably 65 mass % or less, even more preferably 50 mass % or less, and is preferably from 5 mass to 90 mass %, more preferably from 10 mass % to 90 mass %, more preferably from 15 mass % to 85 mass %, more preferably from 15 mass % to 80 mass %, more preferably from 25 mass % to 70 mass %, more preferably from 25 mass % to 65 mass %, even more preferably from 25 mass % to 50 mass %.

<14> The method of producing a solid dispersion according to any one of Items <1> to <13>, wherein the content of the component (C) in the mixture of the component (A), the component (B), and the component (C) is preferably 5 mass % or more, more preferably 10 mass % or more, is preferably 85 mass % or less, more preferably 50 mass or less, even more preferably 30 mass % or less, and is preferably from 5 mass % to 85 mass %, more preferably from 10 mass to 50 mass %, even more preferably from 10 mass % to 30 mass %.

<15> The method of producing a solid dispersion according to any one of Items <1> to <14>, wherein the mass ratio of the component (C) to the component (A), [(C)/(A)], in mixing of the component (A), the component (B), and the component (C) is preferably 0.2 or more, more preferably 0.3 or more, is preferably 19 or less, more preferably 17 or less, more preferably 9 or less, more preferably 6 or less, even more preferably 2 or less, and is preferably from 0.2 to 19, more preferably from 0.2 to 17, more preferably from 0.2 to 9, more preferably from 0.3 to 6, even more preferably from 0.3 to 2.

<16> The method of producing a solid dispersion according to any one of Items <1> to <15>, wherein the mass ratio of the component (C) to the component (B), (C)/(B)], in mixing of the component (A), the component (B), and the component (C) is preferably 0.05 or more, more preferably 0.06 or more, more preferably 0.08 or more, even more preferably 0.11 or more, is preferably 100 or less, more preferably 17 or less, more preferably 4 or less, even more preferably 2 or less, and is preferably from 0.05 to 100, more preferably from 0.05 to 17, more preferably from 0.08 to 4, even more preferably from 0.11 to 2.

<17> The method of producing a solid dispersion according to any one of Items <1> to <16>, wherein the mass ratio of the component (A) to the total of the component (B) and the component (C), [(A)/{(B)+(C)}], in mixing of the component (A), the component (B) and the component (C) is preferably 0.05 or more, more preferably 0.06 or more, more preferably 0.1 or more, even more preferably 0.17 or more, is preferably 3.3 or less, more preferably 3 or less, more preferably 1.1 or less, even more preferably 0.47 or less, and is preferably from 0.05 to 3.3, more preferably from 0.06 to 3, more preferably from 0.1 to 1.1, even more preferably from 0.17 to 0.47.

<18> The method of producing a solid dispersion according to any one of Items <1> to <17>, wherein the step of mixing the component (A), the component (B), and the component (C), followed by melting of the mixture by heating, is carried out using an extruding machine including a screw.

<19> The method of producing a solid dispersion according to Item <18>, wherein the extruding machine including a screw is preferably a single screw extruding machine or a twin screw extruding machine, more preferably a twin screw extruding machine, even more preferably a twin screw extruding machine having two screws that are inserted inside a cylinder so as to be freely rotatable.

<20> The method of producing a solid dispersion according to Item <18> or <19>, wherein the screw rotation speed of the extruding machine is preferably from 30 r/min to 500 r/min, more preferably from 50 r/min to 300 r/min, more preferably from 50 r/min to 250 r/min, even more preferably from 80 r/min to 200 r/min.

<21> The method of producing a solid dispersion according to any one of Items <18> to <20>, wherein the shear rate of the extruding machine is preferably 10 sec$^{-1}$ or more, more preferably from 20 sec$^{-1}$ to 30,000 sec$^{-1}$, even more preferably from 50 sec$^{-1}$ to 3,000 sec$^{-1}$.

<22> The method of producing a solid dispersion according to any one of Items <1> to <21>, wherein the heating is carried out at preferably a temperature equal to or higher than the softening point of the component (B), more preferably a temperature equal to or higher than the melting point of the component (B).

<23> The method of producing a solid dispersion according to any one of Items <1> to <22>, wherein the heating is carried out at a temperature of preferably 75° C. or more, more preferably 100° C. or more, more preferably 115° C. or more, even more preferably 120° C. or more, of preferably 250° C. or less, more preferably 200° C. or less, more preferably 180° C. or less, more preferably 175° C. or less, even more preferably 165° C. or less, and of preferably from 75° C. to 250° C., more preferably from 100° C. to 200° C., more preferably from 115° C. to 180° C., more preferably from 115° C. to 175° C., more preferably from 115° C. to 165° C., even more preferably from 120° C. to 165° C.

<24> The method of producing a solid dispersion according to any one of Items <1> to <23>, wherein the heating is carried out for preferably 30 minutes or less, more preferably 15 minutes or less, even more preferably 10 minutes or less, for preferably 1 minute or more, more preferably 3 minutes or more, even more preferably 5 minutes or more, and for preferably from 1 minute to 30 minutes, more preferably from 3 minutes to 15 minutes, even more preferably from 5 minutes to 10 minutes, after the temperature of the mixture reaches a temperature at which the component (B) melts.

<25> The method of producing a solid dispersion according to any one of Items <1> to <24>, wherein the amorphous component (A) has a crystallinity degree of preferably 50% or less, more preferably 40% or less, more preferably 20% or less, more preferably 10% or less, even more preferably 0%.

<26> The method of producing a solid dispersion according to any one of Items <1> to <25>, wherein the cooling is carried out at preferably a temperature lower than a temperature at which the component (B) melts, more preferably 50° C. or less, even more preferably 30° C. or less.

<27> The method of producing a solid dispersion according to any one of Items <1> to <26>, wherein the cooling rate of the solid dispersion, which is calculated from a time required to lower the heat treatment temperature to 25° C., is preferably 0.1° C./s or more, more preferably 0.2° C./s or more, even more preferably 0.3° C./s or more, and is preferably 100° C./s or less, more preferably 50° C./s or less.

<28> The method of producing a solid dispersion according to any one of Items <1> to <27>, wherein the cooling is carried out for preferably 30 minutes or less, more preferably 20 minutes or less, more preferably 10 minutes or less, even more preferably 5 minutes or less.

<29> The method of producing a solid dispersion according to any one of Items <1> to <28>, wherein the solubility of the component (A) in water (25° C.) in the solid dispersion is preferably 1.5 times or more, more preferably 5 times or more, more preferably 10 times or more, even more preferably 50 times or more, as high as that of an untreated component (A).

<30> The method of producing a solid dispersion according to any one of Items <1> to <29>, wherein the content of water in the solid dispersion is preferably 20 mass % or less, more preferably 10 mass % or less, more preferably 7 mass % or less, even more preferably 5 mass % or less.

<31> The method of producing a solid dispersion according to any one of Items <1> to <30>, wherein the component (A) is ellagic acid.

<32> The method of producing a solid dispersion according to Item <31>, wherein amorphous ellagic acid has a crystallinity degree of preferably 350 or less, more preferably 200 or less.

<33> The method of producing a solid dispersion according to Item <31> or <32>, wherein the solubility of ellagic acid in water (25° C.) in the solid dispersion is preferably 0.04 g/L or more (7.5 times or more as high as that of untreated ellagic acid), more preferably 0.12 g/L or more (22 times or more as high as that of untreated ellagic acid), even more preferably 0.2 g/L or more (37 times or more as high as that of untreated ellagic acid).

<34> A solid dispersion, comprising the amorphous component (A) obtained by the production method of any one of Items <1> to <33>.

<35> The solid dispersion according to Item <34>, wherein the amorphous component (A) has a crystallinity degree of preferably 50% or less, more preferably 40% or less, more preferably 20% or less, more preferably 10% or less, even more preferably 0%.

<36> The solid dispersion according to Item <34> or <35>, wherein the component (A) is ellagic acid.

<37> The solid dispersion according to Item <36>, wherein amorphous ellagic acid has a crystallinity degree of preferably 35% or less, more preferably 20% or less.

<38> A food and drink, comprising the solid dispersion containing the amorphous component (A) of any one of Items <34> to <37>.

EXAMPLES

[Quantification of Hardly Soluble Polyphenols]

Hardly soluble polyphenols were each quantified by a gradient method using a high-performance liquid chromatograph manufactured by Hitachi, Ltd. with a column Cadenza CD-C18 (4.6 mmφ×150 mm, 3 μm) manufactured by Imtakt Corporation at a column temperature of 40° C.

A mobile phase, solution A, was 0.05 mol/L acetic acid aqueous solution, and the other mobile phase, solution B, was acetonitrile. Flow rate was 1.0 mL/min. Gradient conditions are shown below.

| Time (min) | Solution A (%) | Solution B (%) |
| --- | --- | --- |
| 0 | 85 | 15 |
| 20 | 80 | 20 |
| 35 | 10 | 90 |
| 50 | 10 | 90 |
| 50.1 | 85 | 15 |
| 60 | 85 | 15 |

A sample injection volume was 10 μL, and detection was performed on the basis of an absorbance at a wavelength of 320 nm to quantify ferulic acid, an absorbance at a wavelength of 425 nm to quantify curcumin, an absorbance at a wave length of 360 nm to quantify quercetin, an absorbance at a wavelength of 306 nm to quantify resveratrol, an absorbance at a wavelength of 290 nm to quantify naringenin, and an absorbance at a wavelength of 283 nm to quantify other hardly soluble polyphenols.

In addition, ellagic acid was quantified using the same device except that only gradient conditions were set as shown below.

| Time (min) | Solution A (%) | Solution B (%) |
|---|---|---|
| 0 | 99 | 1 |
| 10 | 90 | 10 |
| 20 | 85 | 15 |
| 40 | 10 | 90 |
| 50 | 10 | 90 |
| 50.1 | 85 | 15 |
| 60 | 85 | 15 |

The sample injection volume was 10 µL, and quantification was carried out on the basis of an absorbance at a wavelength of 254 nm.

[Measurement of Weight-Average Molecular Weight of Pectin]

The weight-average molecular weight of pectin was measured by gel permeation chromatography (GPC).

Pectin was added to ion-exchanged water, and pectin was dissolved by heating the resultant to 65° C. After that, the solution of pectin was subjected to measurement by GPC.

The weight-average molecular weight was determined using a 0.2 M phosphate (potassium hydrogen phosphate and disodium hydrogen phosphate) buffer, pH=7/acetonitrile=9/1 under the measurement conditions of: a flow rate of 1.0 mL/min; a column temperature of 40° C.; a sample amount of 2 mg/mL; and a detector wavelength of 210 nm.

[Evaluation of Solubility]

A sample was added to ion-exchanged water at 1 g/L, and the resultant was shaken at 25° C. for 5 minutes. After that, the resultant was filtered with a cellulose acetate filter having a pore size of 0.8 µm, and the concentration of a hardly soluble polyphenol dissolved was measured by the above-mentioned quantification method.

[X-Ray Diffraction Analysis]

An X-ray diffraction intensity was measured using "Mini Flex II" manufactured by Rigaku Corporation under the conditions of: an X-ray source of Cu/Kα-radiation; a tube voltage of 30 kV; a tube current of 15 mA; a measurement range of from 5° to 40° in terms of a diffraction angle; and an X-ray scan speed of 10°/min. A sample for measurement was prepared by compressing a pellet having an area of 400 mm$^2$ and a thickness of 0.5 mm.

Example 1

Ellagic acid (manufactured by KANTO CHEMICAL CO., INC., content of ellagic acid: 98 mass %, the same applies hereinafter), pectin (San-Ei Gen SM-666, esterification rate: 65%, weight-average molecular weight: 210,000), and D(+)-maltose monohydrate (manufactured by Wako Pure Chemical Industries, Ltd., the same applies hereinafter) were mixed at ratios of 25 mass %, 62 mass %, and 13 mass %, respectively, and the mixture was treated using a twin screw extruder (manufactured by Haake Technik) under the conditions of a heating temperature of 180° C., a heating time of 10 minutes, and a screw rotation speed of 80 r/min, and cooled down by blowing cold air for 5 minutes to reach 25° C. (cooling rate: 0.52° C./s). Thus, a solid dispersion was prepared. In this procedure, the inside of the extruding machine was not clogged, and a molded product of the solid dispersion was discharged smoothly.

The concentration of ellagic acid dissolved in the solid dispersion was measured in accordance with the description in the above-mentioned paragraph [Evaluation of Solubility], and was 0.92 g/L. Further, the solid dispersion was stirred with shaking at 25° C. for 3 hours, and then the concentration of ellagic acid dissolved was measured in the same manner as above, and was 0.87 g/L. It found that the high solubility in water was maintained.

Examples 2 and 3

Each solid dispersion was prepared in the same manner as in Example 1 except that the heating temperature was changed to 160° C. or 140° C., and that the cooling time was changed.

Examples 4 to 6

Each solid dispersion was prepared in the same manner as in Example 1 except that the pectin was changed to another pectin (Cargill AYD30T, esterification rate: 71%, weight-average molecular weight: 180,000), that the heating temperature was changed to 180° C., 160° C., or 120° C., and that the cooling time was changed.

Example 7

A solid dispersion was prepared in the same manner as in Example 1 except that pectin (Cargill AYD30T, esterification rate: 71%, weight-average molecular weight: 180,000) and D(+)-maltose monohydrate were mixed at ratios of 47 mass % and 28 mass %, respectively, that the heating temperature was changed to 120° C., and the that cooling time was changed.

Example 8

A solid dispersion was prepared in the same manner as in Example 1 except that the pectin was changed to another pectin (Cargill AYD30T, esterification rate: 71%, weight-average molecular weight: 180,000), D(-)-fructose (manufactured by Wako Pure Chemical Industries, Ltd., the same applies hereinafter) was used instead of D(+)-maltose monohydrate, that the heating temperature was changed to 120° C., and that the cooling time was changed.

Example 9

A solid dispersion was prepared in the same manner as in Example 8 except that pectin and D(-)-fructose were mixed at ratios of 47 mass % and 28 mass %, respectively.

Example 10

A solid dispersion was prepared in the same manner as in Example 1 except that the pectin was changed to another pectin (Cargill SS150, esterification rate: 50%, weight-average molecular weight: 160,000), that the heating temperature was changed to 160° C., and that the cooling time was changed.

Examples 11 and 12

Each solid dispersion was prepared in the same manner as in Example 1 except that the pectin was changed to another pectin (Cargill AYD30T, esterification rate: 71%, weight-average molecular weight: 180,000), that the ratios of ellagic acid, pectin, and D(+)-maltose monohydrate were changed, that the heating temperature was changed to 120° C., and that the cooling time was changed.

Example 13

A solid dispersion was prepared in the same manner as in Example 1 except that the pectin was changed to another pectin (Cargill AYD30T, esterification rate: 71%, weight-average molecular weight: 180,000), that D(+)-glucose (manufactured by Wako Pure Chemical Industries, Ltd.) was used instead of D(+)-maltose monohydrate, that the heating temperature was changed to 150° C., and that the cooling time was changed.

Comparative Example 1

Ellagic acid (25° C.) used in Example 1 was used for evaluation of solubility without additional treatment.

Comparative Example 2

An ellagic acid mixture was obtained by mixing, and at 25° C., with a spatula, ellagic acid, pectin (Cargill AYD30T, esterification rate: 71%, weight-average molecular weight: 180,000), and D(+)-maltose monohydrate at ratios of 25 mass %, 62 mass %, and 13 mass %, respectively.

Comparative Example 3

An ellagic acid mixture was obtained in the same manner as in Comparative Example 2 except that D(−)-fructose was used instead of D(+)-maltose monohydrate.

Comparative Example 4

A mixture obtained by mixing ellagic acid, pectin (Cargill AYD30T, esterification rate: 71%, weight-average molecular weight: 180,000), and D(−)-fructose at ratios of 25 mass %, 35 mass %, and 40 mass %, respectively, was treated in the same manner as in Example 1 under the conditions of a heating temperature of 40° C., a heating time of 5 minutes, and a screw rotation speed of 80 r/min, and cooled down by blowing cold air for 1 minute to reach 25° C. Thus, a solid dispersion was prepared.

Figure 2:
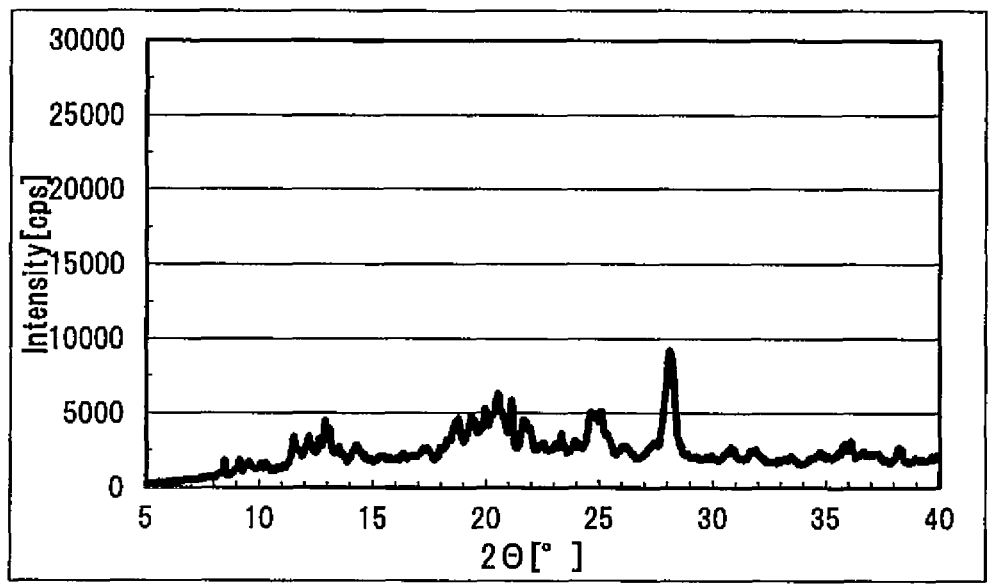
FIG. 2 is a graph for showing the results of powder X-ray diffraction for an ellagic acid mixture of Comparative Example 2.
Figure 3:
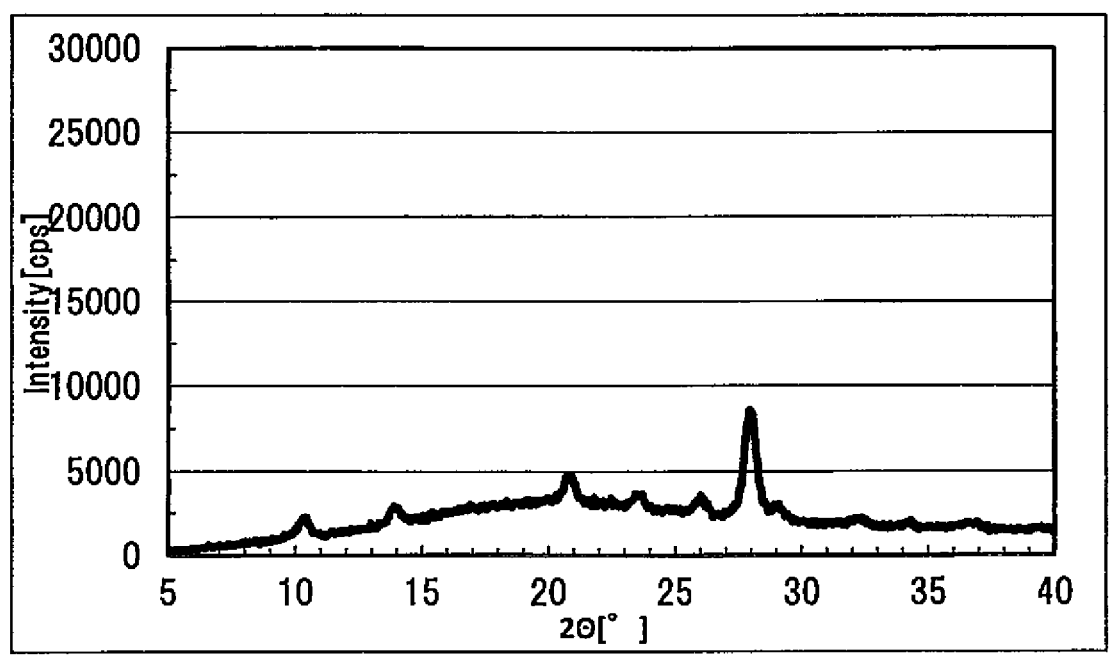
FIG. 3 is a graph for showing the results of powder X-ray diffraction for a solid dispersion of Example 1.

The treatment conditions of Examples and Comparative Examples, and the results of evaluation of solubility of ellagic acid are shown in Table 1. In addition, the results of X-ray diffraction for the ellagic acid of Comparative Example 1, the ellagic acid mixture of Comparative Example 2, and the solid dispersion of Example 1 are shown in FIG. 1 to FIG. 3.

TABLE 1

| | | | Example 1 | Example 2 | Example 3 | Example 4 | Example 5 | Example 6 | Example 7 | Example 8 | Example 9 |
|---|---|---|---|---|---|---|---|---|---|---|---|
| Raw materials | Ellagic acid | [mass %] | 25 | 25 | 25 | 25 | 25 | 25 | 25 | 25 | 25 |
| | Pectin (San-Ei Gen SM-666; HM, molecular weight: 210,000) | [mass %] | 62 | 62 | 62 | 0 | 0 | 0 | 0 | 0 | 0 |
| | Pectin (Cargill AYD30T; HM, molecular weight: 180,000) | [mass %] | 0 | 0 | 0 | 62 | 62 | 62 | 47 | 62 | 47 |
| | Pectin (Cargill SS150; HM, molecular weight: 160,000) | [mass %] | 0 | 0 | 0 | 0 | 0 | 0 | 0 | 0 | 0 |
| | Maltose monohydrate | [mass %] | 13 | 13 | 13 | 13 | 13 | 13 | 28 | 0 | 0 |
| | Fructose | [mass %] | 0 | 0 | 0 | 0 | 0 | 0 | 0 | 13 | 28 |
| | Glucose | [mass %] | 0 | 0 | 0 | 0 | 0 | 0 | 0 | 0 | 0 |
| Treatment conditions | Heating temperature | [° C.] | 180 | 160 | 140 | 180 | 160 | 120 | 120 | 120 | 120 |
| | Heating time | [min] | 10 | 10 | 10 | 10 | 10 | 10 | 10 | 10 | 10 |
| | Screw rotation speed of extruder | [r/min] | 80 | 80 | 80 | 80 | 80 | 80 | 80 | 80 | 80 |
| | Extruder torque | [N · m] | 1.3 | 2.1 | 4 | 1.3 | 1.2 | 1.3 | 0.12 | 2.1 | 0.12 |
| | Cooling temperature | [° C.] | 25 | 25 | 25 | 25 | 25 | 25 | 25 | 25 | 25 |
| | Cooling time | [min] | 5 | 4 | 3 | 5 | 4 | 3 | 3 | 3 | 3 |
| | Amount of ellagic acid dissolved | [g/L] | 0.92 | 0.94 | 0.89 | 0.67 | 0.79 | 0.42 | 0.45 | 0.39 | 0.39 |

TABLE 1-continued

|  |  |  | Example 1 | Example 2 | Example 3 | Example 4 | Example 5 | Example 6 | Example 7 | Example 8 | Example 9 |
|---|---|---|---|---|---|---|---|---|---|---|---|
|  |  |  | Example 10 | Example 11 | Example 12 | Example 13 | Comparative Example 1 | Comparative Example 2 | Comparative Example 3 | Comparative Example 4 |
| Raw materials | Ellagic acid | [mass %] | 25 | 50 | 75 | 25 | 100 | 25 | 25 | 25 |
|  | Pectin (San-Ei Gen SM-666; HM, molecular weight: 210,000) | [mass %] | 0 | 0 | 0 | 0 | 0 | 0 | 0 | 0 |
|  | Pectin (Cargill AYD30T; HM, molecular weight: 180,000) | [mass %] | 0 | 25 | 5 | 62 | 0 | 62 | 62 | 35 |
|  | Pectin (Cargill SS150; HM, molecular weight: 160,000) | [mass %] | 62 | 0 | 0 | 0 | 0 | 0 | 0 | 0 |
|  | Maltose monohydrate | [mass %] | 13 | 25 | 20 | 0 | 0 | 13 | 0 | 0 |
|  | Fructose | [mass %] | 0 | 0 | 0 | 0 | 0 | 0 | 13 | 40 |
|  | Glucose | [mass %] | 0 | 0 | 0 | 13 | 0 | 0 | 0 | 0 |
| Treatment conditions | Heating temperature | [° C.] | 160 | 120 | 120 | 150 | Untreated | Untreated | Untreated | 40 |
|  | Heating time | [min] | 10 | 10 | 10 | 10 | Untreated | Untreated | Untreated | 5 |
|  | Screw rotation speed of extruder | [r/min] | 80 | 80 | 80 | 80 | Untreated | Untreated | Untreated | 80 |
|  | Extruder torque | [N · m] | 1.5 | 2.3 | 2.4 | 1.3 | Untreated | Untreated | Untreated | 5 |
|  | Cooling temperature | [° C.] | 25 | 25 | 25 | 25 | Untreated | Untreated | Untreated | 25 |
|  | Cooling time | [min] | 4 | 3 | 3 | 3 | Untreated | Untreated | Untreated | 1 |
| Amount of ellagic acid dissolved |  | [g/L] | 0.95 | 0.37 | 0.26 | 0.9 | 0.0053 | 0.052 | 0.059 | 0.066 |

As is apparent from Table 1, the solid dispersions each containing ellagic acid having improved solubility in water were obtained in Examples 1 to 13. In addition, as is apparent from FIG. 3, ellagic acid in the solid dispersion of Example 1 was found to have a crystallinity degree of 17%, and the degree indicates that the ellagic acid became amorphous. Meanwhile, as shown in FIG. 1 and FIG. 2, in the ellagic acid of Comparative Example 1 and in the ellagic acid mixture of Comparative Example 2, crystallinity degrees of ellagic acid were found to be 87% and 52%, respectively, and the degrees suggest that the products each had high crystallinity.

Example 14

The pectin was changed to another pectin (Cargill 805C, esterification rate: 35%, weight-average molecular weight: 220,000), and a mixture of ellagic acid, pectin, and D(+)-maltose monohydrate was treated in the same manner as in Example 1 under the conditions of a heating temperature of 110° C., a heating time of 10 minutes, and a screw rotation speed of 80 r/min, and cooled down by blowing cold air for 3 minutes to reach 25° C. Thus, a solid dispersion was prepared.

Example 15

A solid dispersion was prepared in the same manner as in Example 14 except that the pectin was changed to another pectin (Cargill AYS407C, esterification rate: 29%, weight-average molecular weight: 220,000).

Example 16

A solid dispersion was prepared in the same manner as in Example 14 except that the pectin was changed to another pectin (Cargill LMSN325, esterification rate: 30%, weight-average molecular weight: 220,000).

Examples 17 and 18

Each solid dispersion was prepared in the same manner as in Example 14 except that pectin (Cargill LMQS400C, esterification rate: 30%, weight-average molecular weight: 260,000) and D(+)-maltose monohydrate were mixed at ratios of 54 mass % and 21 mass %, respectively, and that the heating temperature was changed to 110° C. or 140° C.

Example 19

A solid dispersion was prepared in the same manner as in Example 14 except that the pectin was changed to another pectin (Cargill OF445C, esterification rate: 28%, weight-average molecular weight: 250,000).

The treatment conditions of Examples and Comparative Examples, and the results of evaluation of solubility of ellagic acid are shown in Table 2.

TABLE 2

|  |  |  | Example 14 | Example 15 | Example 16 | Example 17 | Example 18 | Example 19 |
|---|---|---|---|---|---|---|---|---|
| Raw materials | Ellagic acid | [mass %] | 25 | 25 | 25 | 25 | 25 | 25 |
|  | Pectin (Cargill 805C; LM, molecular weight: 220,000) | [mass %] | 62 | 0 | 0 | 0 | 0 | 0 |
|  | Pectin (Cargill AYS407C; LM, molecular weight: 220,000) | [mass %] | 0 | 62 | 0 | 0 | 0 | 0 |
|  | Pectin (Cargill LMSN325; LM, molecular weight: 220,000) | [mass %] | 0 | 0 | 62 | 0 | 0 | 0 |
|  | Pectin (Cargill LMQS400C; LM, molecular weight: 260,000) | [mass %] | 0 | 0 | 0 | 54 | 54 | 0 |
|  | Pectin (Cargill OF445C; LM, molecular weight: 250,000) | [mass %] | 0 | 0 | 0 | 0 | 0 | 62 |
|  | Maltose monohydrate | [mass %] | 13 | 13 | 13 | 21 | 21 | 13 |
| Treatment conditions | Heating temperature | [° C.] | 110 | 110 | 110 | 110 | 140 | 110 |
|  | Heating time | [min] | 10 | 10 | 10 | 10 | 10 | 10 |
|  | Screw rotation speed of extruder | [r/min] | 80 | 80 | 80 | 80 | 80 | 80 |
|  | Extruder torque | [N · m] | 4.5 | 0.8 | 0.4 | 1.3 | 3.6 | 2.4 |
|  | Cooling temperature | [° C.] | 25 | 25 | 25 | 25 | 25 | 25 |
|  | Cooling time | [min] | 3 | 3 | 3 | 3 | 3 | 3 |
| Amount of ellagic acid dissolved |  | [g/L] | 0.69 | 0.64 | 0.65 | 0.87 | 1.0 | 0.52 |

Example 20

Polyglutamic acid (manufactured by Meiji Food Materia Co., Ltd., content of polyglutamic acid: 70 mass %) was used instead of pectin, and a mixture obtained by mixing ellagic acid, polyglutamic acid, and D(+)-maltose monohydrate at ratios of 25 mass %, 28 mass %, and 47 mass %, respectively, was treated in the same manner as in Example 1 under the conditions of a heating temperature of 120° C. a heating time of 10 minutes, and a screw rotation speed of 80 r/min, and cooled down by blowing cold air for 3 minutes to reach 25° C. Thus, a solid dispersion was prepared.

Example 21

A solid dispersion was prepared in the same manner as in Example except that potassium alginate (manufactured by KIMICA Corporation, K-1, content of potassium alginate: 100 mass %) was used instead of polyglutamic acid.

Example 22

A solid dispersion was prepared in the same manner as in Example 20 except that inulin (manufactured by Wako Pure Chemical Industries, Ltd., content of inulin: 99 mass %) was used instead of polyglutamic acid.

Example 23

A solid dispersion was prepared in the same manner as in Example 20 except that λ-carrageenan (manufactured by Wako Pure Chemical Industries, Ltd., content of λ-carrageenan: 60 mass % or more) was used instead of polyglutamic acid.

Example 24

A solid dispersion was prepared in the same manner as in Example 20 except that soy protein (manufactured by Junsei Chemical Co., Ltd., content of soy protein: 78 mass % or more) was used instead of polyglutamic acid.

Example 25

A solid dispersion was prepared in the same manner as in Example 20 except that polygalacturonic acid (manufactured by Alfa Aesar, content of polygalacturonic acid: 65 mass % or more) was used instead of polyglutamic acid.

The treatment conditions of Examples and the results of evaluation of solubility of ellagic acid are shown in Table 3.

TABLE 3

|  |  |  | Example 20 | Example 21 | Example 22 | Example 23 | Example 24 | Example 25 |
|---|---|---|---|---|---|---|---|---|
| Raw materials | Ellagic acid | [mass %] | 25 | 25 | 25 | 25 | 25 | 25 |
|  | Polyglutamic acid | [mass %] | 28 | 0 | 0 | 0 | 0 | 0 |
|  | Potassiumalginate | [mass %] | 0 | 28 | 0 | 0 | 0 | 0 |
|  | Inulin | [mass %] | 0 | 0 | 28 | 0 | 0 | 0 |
|  | λ-Carrageenan | [mass %] | 0 | 0 | 0 | 28 | 0 | 0 |
|  | Soy protein | [mass %] | 0 | 0 | 0 | 0 | 28 | 0 |
|  | Polygalacturonic acid | [mass %] | 0 | 0 | 0 | 0 | 0 | 28 |
|  | Maltose monohydrate | [mass %] | 47 | 47 | 47 | 47 | 47 | 47 |

TABLE 3-continued

|  |  |  | Example 20 | Example 21 | Example 22 | Example 23 | Example 24 | Example 25 |
|---|---|---|---|---|---|---|---|---|
| Treatment conditions | Heating temperature | [° C.] | 120 | 120 | 120 | 120 | 120 | 120 |
|  | Heating time | [min] | 10 | 10 | 10 | 10 | 10 | 10 |
|  | Screw rotation speed of extruder | [r/min] | 80 | 80 | 80 | 80 | 80 | 80 |
|  | Extruder torque | [N · m] | 0.5 | 0.4 | 0.2 | 0.8 | 1 | 0.2 |
|  | Cooling temperature | [° C.] | 25 | 25 | 25 | 25 | 25 | 25 |
|  | Cooling time | [min] | 3 | 3 | 3 | 3 | 3 | 3 |
| Amount of ellagic acid dissolved |  | [g/L] | 0.41 | 0.39 | 0.47 | 0.71 | 0.31 | 0.28 |

As is apparent from Table 2 and Table 3, solid dispersions each containing ellagic acid having improved solubility in water were also obtained in Examples 14 to 25. In all of Examples, the inside of the extruding machine was not clogged, and molded products of the solid dispersions were discharged smoothly.

Example 26

A mixture obtained by mixing quercetin dihydrate (manufactured by Alfa Aesar, content of quercetin dihydrate: 97 mass %), pectin (Cargill AYD30T, esterification rate: 71%, weight-average molecular weight: 180,000), and D(+)-maltose monohydrate at ratios of 25 mass %, 62 mass %, and 13 mass %, respectively, was treated in the same manner as in Example 1 under the conditions of a heating temperature of 120° C., a heating time of 10 minutes, and a screw rotation speed of 80 r/min, and cooled down by blowing cold air for 3 minutes to reach 25° C. Thus, a solid dispersion was prepared.

Example 27

A solid dispersion was prepared in the same manner as in Example 26 except that the pectin was changed to another pectin (Cargill AYS407C, esterification rate: 29%, weight-average molecular weight: 220,000), and that the heating temperature was changed to 110° C.

Example 28

A solid dispersion was prepared in the same manner as in Example 26 except that the pectin was changed to another pectin (Cargill OF327C, esterification rate: 36%, weight-average molecular weight: 220,000), and that the heating temperature was changed to 110° C.

Comparative Example 5

Quercetin dihydrate (25° C.) used in Example 26 was used without additional treatment for evaluation of solubility.

The treatment conditions of Examples and Comparative Example, and the results of evaluation of solubility of quercetin dihydrate are shown in Table 4.

TABLE 4

|  |  |  | Example 26 | Example 27 | Example 28 | Comparative Example 5 |
|---|---|---|---|---|---|---|
| Raw materials | Quercetin dihydrate | [mass %] | 25 | 25 | 25 | 100 |
|  | Pectin (Cargill AYD30T; HM, molecular weight: 180,000) | [mass %] | 62 | 0 | 0 | 0 |
|  | Pectin (Cargill AYS407C; LM, molecular weight: 220,000) | [mass %] | 0 | 62 | 0 | 0 |
|  | Pectin (Cargill OF327C; LM, molecular weight: 220,000) | [mass %] | 0 | 0 | 62 | 0 |
|  | Maltose monohydrate | [mass %] | 13 | 13 | 13 | 0 |
| Treatment conditions | Heating temperature | [° C.] | 120 | 110 | 110 | Untreated |
|  | Heating time | [min] | 10 | 10 | 10 | Untreated |
|  | Screw rotation speed of extruder | [r/min] | 80 | 80 | 80 | Untreated |
|  | Extruder torque | [N · m] | 0.5 | 0.5 | 0.5 | Untreated |
|  | Cooling temperature | [° C.] | 25 | 25 | 25 | Untreated |
|  | Cooling time | [min] | 3 | 3 | 3 | Untreated |
| Amount of quercetin dissolved |  | [g/L] | 1.0 | 0.1 | 0.2 | 0.005 |

Examples 29 to 31

A mixture obtained by mixing ferulic acid (manufactured by Tsuno Rice Fine Chemicals Co., Ltd., content of ferulic acid: 98 mass %), pectin (Cargill AYD30T, esterification rate: 71%, weight-average molecular weight: 180,000), and D(+)-maltose monohydrate at ratios of 25 mass %, 62 mass %, and 13 mass %, respectively, was treated in the same manner as in Example 1 under the conditions of a heating temperature of 140° C., 130° C., or 120° C., a heating time of 10 minutes, and a screw rotation speed of 80 r/min, and cooled down by blowing cold air for 3 minutes to reach 25° C. Thus, solid dispersions were prepared.

Comparative Example 6

Ferulic acid (25° C.) used in Example 29 was used without additional treatment for evaluation of solubility.

The treatment conditions of Examples and Comparative Example, and the results of evaluation of solubility of ferulic acid are shown in Table 5.

TABLE 5

|  |  |  | Example 29 | Example 30 | Example 31 | Comparative Example 6 |
|---|---|---|---|---|---|---|
| Raw materials | Ferulic acid | [mass %] | 25 | 25 | 25 | 100 |
|  | Pectin (Cargill AYD30T; HM, molecular weight: 180,000) | [mass %] | 62 | 62 | 62 | 0 |
|  | Maltose monohydrate | [mass %] | 13 | 13 | 13 | 0 |
| Treatment conditions | Heating temperature | [° C.] | 140 | 130 | 120 | Untreated |
|  | Heating time | [min] | 10 | 10 | 10 | Untreated |
|  | Screw rotation speed of extruder | [r/min] | 80 | 80 | 80 | Untreated |
|  | Extruder torque | [N·m] | 0.4 | 0.3 | 0.5 | Untreated |
|  | Cooling temperature | [° C.] | 25 | 25 | 25 | Untreated |
|  | Cooling time | [min] | 3 | 3 | 3 | Untreated |
| Amount of ferulic acid dissolved |  | [g/L] | 1.0 | 1.0 | 1.0 | 0.66 |

Example 32

A mixture obtained by mixing curcumin (manufactured by Tokyo Chemical Industry Co., Ltd., content of curcumin: 97 mass %), pectin (Cargill AYD30T, esterification rate: 71%, weight-average molecular weight: 180,000), and D(+)-maltose monohydrate at ratios of 25 mass %, 62 mass %, and 13 mass %, respectively, was treated in the same manner as in Example 1 under the conditions of: a heating temperature of 120° C., a heating time of 10 minutes, and a screw rotation speed of 80 r/min, and cooled down by blowing cold air for 3 minutes to reach 25° C. Thus, a solid dispersion was prepared.

Comparative Example 7

Curcumin (25° C.) used in Example 32 was used without additional treatment for evaluation of solubility.

The treatment conditions of Example and Comparative Example, and the results of evaluation of solubility of curcumin are shown in Table 6.

TABLE 6

|  |  |  | Example 32 | Comparative Example 7 |
|---|---|---|---|---|
| Raw materials | Curcumin | [mass %] | 25 | 100 |
|  | Pectin (Cargill AYD30T; HM, molecular weight: 180,000) | [mass %] | 62 | 0 |
|  | Maltose monohydrate | [mass %] | 13 | 0 |
| Treatment conditions | Heating temperature | [° C.] | 120 | Untreated |
|  | Heating time | [min] | 10 | Untreated |
|  | Screw rotation speed of extruder | [r/min] | 80 | Untreated |
|  | Extruder torque | [N·m] | 1.2 | Untreated |
|  | Cooling temperature | [° C.] | 25 | Untreated |
|  | Cooling time | [min] | 3 | Untreated |
| Amount of curcumin dissolved |  | [g/L] | 0.3 | 0.001 |

Example 33

A mixture obtained by mixing nobiletin (manufactured by INDOFINE Chemical Company, Inc., content of nobiletin: 96 mass %), pectin (Cargill AYS407C, esterification rate: 290, weight-average molecular weight: 220,000), and D(+)-maltose monohydrate at ratios of 20 mass %, 67 mass %, and 13 mass %, respectively, was treated in the same manner as in Example 1 under the conditions of a heating temperature of 120° C., a heating time of 10 minutes, and a screw rotation speed of 80 r/min, and cooled down by blowing cold air for 3 minutes to reach 25° C. Thus, a solid dispersion was prepared.

Comparative Example 8

Nobiletin (25° C.) used in Example 33 was used without additional treatment for evaluation of solubility.

The treatment conditions of Example and Comparative Example, and the results of evaluation of solubility of nobiletin are shown in Table 7.

TABLE 7

|  |  |  | Example 33 | Comparative Example 8 |
|---|---|---|---|---|
| Raw materials | Nobiletin | [mass %] | 20 | 100 |
|  | Pectin (Cargill AYS407C; LM, molecular weight: 220,000) | [mass %] | 67 | 0 |
|  | Maltose monohydrate | [mass %] | 13 | 0 |
| Treatment conditions | Heating temperature | [° C.] | 120 | Untreated |
|  | Heating time | [min] | 10 | Untreated |
|  | Screw rotation speed of extruder | [r/min] | 80 | Untreated |
|  | Extruder torque | [N·m] | 1.5 | Untreated |
|  | Cooling temperature | [° C.] | 25 | Untreated |
|  | Cooling time | [min] | 3 | Untreated |
| Amount of nobiletin dissolved |  | [g/L] | 0.3 | 0.007 |

Example 34

A mixture obtained by mixing sesamin (manufactured by Kadoya Sesame Mills Incorporated, content of sesamin: 99 mass %), pectin (Cargill AYD30T, esterification rate: 71%, weight-average molecular weight: 180,000), and D(+)-maltose monohydrate at ratios of 20 mass %, 67 mass %, and 13 mass %, respectively, was treated in the same manner as in Example 1 under the conditions of a heating temperature of 160° C., a heating time of 10 minutes, and a screw rotation speed of 80 r/min, and cooled down by blowing cold air for 3 minutes to reach 25° C. Thus, a solid dispersion was prepared.

Comparative Example 9

Sesamin (25° C.) used in Example 34 was used without additional treatment for evaluation of solubility.

The treatment conditions of Example and Comparative Example, and the results of evaluation of solubility of sesamin are shown in Table 8.

TABLE 8

| | | | Example 34 | Comparative Example 9 |
|---|---|---|---|---|
| Raw materials | Sesamin | [mass %] | 20 | 100 |
| | Pectin (Cargill AYD30T; HM, molecular weight: 180,000) | [mass %] | 67 | 0 |
| | Maltose monohydrate | [mass %] | 13 | 0 |
| Treatment conditions | Heating temperature | [° C.] | 160 | Untreated |
| | Heating time | [min] | 10 | Untreated |
| | Screw rotation speed of extruder | [r/min] | 80 | Untreated |
| | Extruder torque | [N · m] | 1.5 | Untreated |
| | Cooling temperature | [° C.] | 25 | Untreated |
| | Cooling time | [min] | 3 | Untreated |
| | Amount of sesamin dissolved | [g/L] | 0.043 | 0.0001 |

Example 35

A mixture obtained by mixing soy isoflavone (manufactured by Fuji Oil Co., Ltd., SOYAFLAVONE HG, content of soy isoflavone: 50 mass %), pectin (Cargill AYD30T, esterification rate: 71%, weight-average molecular weight: 180,000), and D(+)-maltose monohydrate at ratios of 25 mass %, 62 mass %, and 13 mass %, respectively, was treated in the same manner as in Example 1 under the conditions of a heating temperature of 120° C., a heating time of 10 minutes, and a screw rotation speed of 80 r/min, and cooled down by blowing cold air for 3 minutes to reach 25° C. Thus, a solid dispersion was prepared.

Comparative Example 10

Soy isoflavone (25° C.) used in Example 35 was used without additional treatment for evaluation of solubility.

The treatment conditions of Example and Comparative Example, and the results of evaluation of solubility of soy isoflavone are shown in Table 9.

TABLE 9

| | | | Example 35 | Comparative Example 10 |
|---|---|---|---|---|
| Raw materials | Soy isoflavone | [mass %] | 25 | 100 |
| | Pectin (Cargill AYD30T; HM, molecular weight: 180,000) | [mass %] | 62 | 0 |
| | Maltose monohydrate | [mass %] | 13 | 0 |
| Treatment conditions | Heating temperature | [° C.] | 120 | Untreated |
| | Heating time | [min] | 10 | Untreated |
| | Rotation speed of extruder screw | [r/min] | 80 | Untreated |
| | Extruder torque | [N · m] | 0.2 | Untreated |
| | Cooling temperature | [° C.] | 25 | Untreated |
| | Cooling time | [min] | 3 | Untreated |
| | Amount of soy isoflavone dissolved | [g/L] | 0.335 | 0.033 |

Example 36

A mixture obtained by mixing resveratrol (manufactured by Tokyo Chemical Industry Co., Ltd., content of resveratrol: 99 mass %), pectin (Cargill AYD30T, esterification rate: 71%, weight-average molecular weight: 180,000), and D(+)-maltose monohydrate at ratios of 25 mass %, 62 mass %, and 13 mass %, respectively, was treated in the same manner as in Example 1 under the conditions of a heating temperature of 150° C., a heating time of 10 minutes, and a screw rotation speed of 80 r/min, and cooled down by blowing cold air for 3 minutes to reach 25° C. Thus, a solid dispersion was prepared.

Example 37

A solid dispersion was prepared in the same manner as in Example 36 except that the pectin was changed to another pectin (Cargill AYS407C, esterification rate: 29%, weight-average molecular weight: 220,000), and that the heating temperature was changed to 110° C.

Example 38

A solid dispersion was prepared in the same manner as in Example 36 except that the pectin was changed to another pectin (Cargill OF327C, esterification rate: 36%, weight-average molecular weight: 220,000), and that the heating temperature was changed to 110° C.

Comparative Example 11

Resveratrol (25° C.) used in Example 36 was used without additional treatment for evaluation of solubility.

The treatment conditions of Examples and Comparative Example, and the results of evaluation of solubility of resveratrol are shown in Table 10.

TABLE 10

| | | | Example 36 | Example 37 | Example 38 | Comparative Example 11 |
|---|---|---|---|---|---|---|
| Raw materials | Resveratrol | [mass %] | 25 | 25 | 25 | 100 |
| | Pectin (Cargill AYD30T; HM, molecular weight: 180,000) | [mass %] | 62 | 0 | 0 | 0 |
| | Pectin (Cargill AYS407C; LM, molecular weight: 220,000) | [mass %] | 0 | 62 | 0 | 0 |
| | Pectin (Cargill OF327C; LM, molecular weight: 220,000) | [mass %] | 0 | 0 | 62 | 0 |
| | Maltose monohydrate | [mass %] | 13 | 13 | 13 | 0 |

TABLE 10-continued

|  |  |  | Example 36 | Example 37 | Example 38 | Comparative Example 11 |
|---|---|---|---|---|---|---|
| Treatment conditions | Heating temperature | [° C.] | 150 | 110 | 110 | Untreated |
|  | Heating time | [min] | 10 | 10 | 10 | Untreated |
|  | Screw rotation speed of extruder | [r/min] | 80 | 80 | 80 | Untreated |
|  | Extruder torque | [N · m] | 0.2 | 0.2 | 0.2 | Untreated |
|  | Cooling temperature | [° C.] | 25 | 25 | 25 | Untreated |
|  | Cooling time | [min] | 3 | 3 | 3 | Untreated |
|  | Amount of resveratrol dissolved | [g/L] | 0.34 | 0.25 | 0.24 | 0.03 |

As is apparent from Table 4 to Table 10, solid dispersions each containing a hardly soluble polyphenol other than ellagic acid, having improved solubility in water were obtained. In all of Examples the inside of the extruding machine was not clogged, and molded products of the solid dispersions were discharged smoothly.

Examples 39 to 48

A mixture obtained by mixing ellagic acid, pectin (Cargill AYS407C, esterification rate: 29%, weight-average molecular weight: 220,000), and D (+)-maltose monohydrate at ratios shown in Table 11, respectively, was treated in the same manner as in Example 1 under the conditions of a heating temperature of 110° C., a heating time of 10 minutes, and a screw rotation speed of 80 r/min, and cooled down by blowing cold air for 3 minutes to reach 25° C. Thus, solid dispersions were prepared.

The treatment conditions of Examples and the results of evaluation of solubility of ellagic acid are shown in Table 11.

As is apparent from Table 11, solid dispersions each containing ellagic acid having improved solubility in water were obtained.

Examples 49 to 54

A mixture obtained by mixing naringenin (manufactured by Tokyo Chemical Industry Co., Ltd., content of naringenin: 98 mass %), pectin (Cargill AYS407C esterification rate: 29%, weight-average molecular weight: 220,000), and D(+)-maltose monohydrate at ratios shown in Table 12, respectively, was treated in the same manner as in Example 1 under the conditions of a heating temperature of 110° C., a heating time of 3 minutes or 10 minutes, and a screw rotation speed of 80 r/min, and cooled down by blowing cold air for 3 minutes to reach 25° C. Thus, solid dispersions were prepared.

Example 55

A solid dispersion was prepared in the same manner as in Example 49 except that the screw rotation speed was changed to 160 r/min.

Comparative Example 12

Naringenin (25° C.) used in Example 49 was used without additional treatment for evaluation of solubility.

The treatment conditions of Examples and Comparative Example, and the results of evaluation of solubility of naringenin are shown in Table 12.

TABLE 11

|  |  |  | Example 39 | Example 40 | Example 41 | Example 42 | Example 43 | Example 44 | Example 45 | Example 46 | Example 47 | Example 48 |
|---|---|---|---|---|---|---|---|---|---|---|---|---|
| Raw materials | Ellagic acid | [mass %] | 25 | 25 | 10 | 10 | 10 | 10 | 42 | 34 | 17 | 13 |
|  | Pectin (Cargill AYS407C; LM, molecular weight: 220,000) | [mass %] | 66 | 69 | 77 | 81 | 84 | 85 | 48 | 55 | 69 | 73 |
|  | Maltose monohydrate | [mass %] | 9 | 6 | 13 | 9 | 6 | 5 | 10 | 11 | 14 | 14 |
| Treatment conditions | Heating temperature | [° C.] | 110 | 110 | 110 | 110 | 110 | 110 | 110 | 110 | 110 | 110 |
|  | Heating time | [min] | 10 | 10 | 10 | 10 | 10 | 10 | 10 | 10 | 10 | 10 |
|  | Screw rotation speed of extruder | [r/min] | 80 | 80 | 80 | 80 | 80 | 80 | 80 | 80 | 80 | 80 |
|  | Extruder torque | [N · m] | 2.1 | 4.6 | 0.7 | 1.7 | 2.0 | 3.5 | 4.7 | 1.6 | 0.5 | 0.4 |
|  | Cooling temperature | [° C.] | 25 | 25 | 25 | 25 | 25 | 25 | 25 | 25 | 25 | 25 |
|  | Cooling time | [min] | 3 | 3 | 3 | 3 | 3 | 3 | 3 | 3 | 3 | 3 |
| Amount of ellagic acid dissolved | | [g/L] | 0.5 | 0.78 | 0.45 | 0.5 | 0.51 | 0.56 | 0.84 | 0.52 | 0.46 | 0.43 |

TABLE 12

| | | | Example 49 | Example 50 | Example 51 | Example 52 | Example 53 | Example 54 | Example 55 | Comparative Example 12 |
|---|---|---|---|---|---|---|---|---|---|---|
| Raw materials | Naringenin | [mass %] | 25 | 25 | 17 | 13 | 34 | 42 | 25 | 100 |
| | Pectin (Cargill AYS407C; LM, molecular weight: 220,000) | [mass %] | 62 | 62 | 69 | 73 | 55 | 48 | 62 | 0 |
| | Maltose monohydrate | [mass %] | 13 | 13 | 14 | 14 | 11 | 10 | 13 | 0 |
| Treatment conditions | Heating temperature | [° C.] | 110 | 110 | 110 | 110 | 110 | 110 | 110 | Untreated |
| | Heating time | [min] | 10 | 3 | 10 | 10 | 10 | 10 | 10 | Untreated |
| | Screw rotation speed of extruder | [r/min] | 80 | 80 | 80 | 80 | 80 | 80 | 160 | Untreated |
| | Extruder torque | [N · m] | 0.7 | 0.4 | 0.5 | 0.5 | 1.3 | 2.3 | 1.7 | Untreated |
| | Cooling temperature | [° C.] | 25 | 25 | 25 | 25 | 25 | 25 | 25 | Untreated |
| | Cooling time | [min] | 3 | 3 | 3 | 3 | 3 | 3 | 3 | Untreated |
| Amount of naringenin dissolved | | [g/L] | 0.21 | 0.16 | 0.2 | 0.18 | 0.26 | 0.24 | 0.2 | 0.008 |

As is apparent from Table 12, solid dispersions each containing naringenin having improved solubility in water were obtained.

The invention claimed is:

1. A method of producing a solid dispersion containing an amorphous hardly soluble polyphenol, comprising the steps of:
mixing (A) a polyphenol having a solubility in water at 25° C. of 5 g/L or less, wherein said polyphenol is ellagic acid, (B) pectin, and (C) at least one selected from the group consisting of maltose, fructose, and glucose,
wherein the content of the component (A) in the mixture is from 5 mass % to 75 mass %, the content of the component (B) in the mixture is from 5 mass % to 80 mass %, and the content of the component (C) in the mixture is from 5 mass % to 85 mass %, and a mass ratio of the component (A) to a total of the component (B) and the component (C), [(A)/{(B)+(C)}], is from 0.17 to 0.47,
followed by
melting of the mixture by heating at a temperature of from 75° C. to 250° C.; and
solidifying the molten product by cooling to provide said solid dispersion.

2. The method of producing a solid dispersion according to claim 1, wherein a mass ratio of the component (C) to the component (A), [(C)/(A)], in mixing of the component (A), the component (B), and the component (C) is from 0.2 to 19.

3. The method of producing a solid dispersion according to claim 1, wherein a mass ratio of the component (C) to the component (B), [(C)/(B)], in mixing of the component (A), the component (B), and the component (C) is from 0.05 to 100.

4. The method of producing a solid dispersion according to claim 1, wherein the step of mixing the component (A), the component (B), and the component (C), followed by melting of the mixture by heating, is carried out using an extruding machine including a screw.

5. The method of producing a solid dispersion according to claim 1, wherein the component (B) pectin has an esterification rate of 50% or more.

* * * * *